US 6,730,622 B2

(12) United States Patent
Curro et al.

(10) Patent No.: US 6,730,622 B2
(45) Date of Patent: May 4, 2004

(54) ELECTRICAL CABLE

(75) Inventors: John Joseph Curro, Cincinnati, OH (US); Douglas Herrin Benson, West Harrison, IN (US); John Brian Strube, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 81 days.

(21) Appl. No.: 09/886,894

(22) Filed: Jun. 21, 2001

(65) Prior Publication Data

US 2002/0062974 A1 May 30, 2002

Related U.S. Application Data

(63) Continuation-in-part of application No. PCT/US00/34746, filed on Dec. 20, 2000, and a continuation-in-part of application No. 09/584,676, filed on May 31, 2000, and a continuation-in-part of application No. 09/467,938, filed on Dec. 21, 1999.

(51) Int. Cl.[7] .......................... D04H 1/00; D04H 3/00; D04H 5/00; D04H 13/00; B32B 5/26; B32B 27/12; H01B 7/00
(52) U.S. Cl. ...................... 442/336; 442/376; 442/377; 442/379; 442/381; 442/394; 174/113 R; 174/119 R; 174/120 R; 174/121 R
(58) Field of Search .......................... 174/68.1, 110 R, 174/113 R, 119 R, 120 R, 121 R; 442/336, 376, 377, 379, 381, 394; 156/229, 184

(56) References Cited

U.S. PATENT DOCUMENTS

| 4,000,348 A | | 12/1976 | Harlow | |
|---|---|---|---|---|
| 4,924,037 A | * | 5/1990 | Ainsworth et al. | 174/117 F |
| 5,304,741 A | * | 4/1994 | Proulx | 174/117 FF |
| 5,744,756 A | * | 4/1998 | Springer et al. | 174/110 N |

* cited by examiner

Primary Examiner—Cheryl A. Juska
Assistant Examiner—Jeremy R. Pierce
(74) Attorney, Agent, or Firm—Roddy M. Bullock; Angela Marie Stone

(57) ABSTRACT

An electrical cable of the present invention comprises a plurality of spaced, parallel flat conductors. Each of the plurality of flat conductors was previously integral with each immediately adjacent flat conductor. A dielectric material is holds the conductors in the spaced, parallel relationship. The dielectric material can be a polymer film, a nonwoven, or other polymer materials such as PTFE, or expanded PTFE. The cable of the present invention is made by providing first and second webs of dielectric materials and a third sheet of conductive material. The first and second web materials are bonded to the third sheet of conductive material in a face-to-face layered relationship thereby forming a bonded laminate. The bonded laminate is then incrementally stretched to separate the sheet of conductive material in to spaced, parallel flat conductors.

7 Claims, 4 Drawing Sheets

ELECTRICAL CABLE

CROSS REFERENCE TO RELATED APPLICATIONS

This application is: a continuation-in-part and claims priority of prior application PCT International Application Serial No. US00/34746 (Case 7897R2) which designates the US, will publish in English, and was filed Dec. 20, 2000 in the names of Curro et al.; and a continuation-in-part and claims priority of prior application Ser. No. 09/584676 (Case 7897R2), filed May 31, 2000 in the names of Curro et al.; and a continuation-in-part and claims priority of prior application Ser. No. 09/467938 (Case 7897), filed Dec. 21, 1999 in the names of Curro et al.

FIELD OF THE INVENTION

This invention relates to a conductive webs and fabrics, and more particularly to a laminate web wherein at least a central layer is conductive. In some embodiments the central layer comprises a plurality of spaced, parallel conductors.

BACKGROUND OF THE INVENTION

Electrical cables are known in the art. Electrical cables can be used for power transmission or for signal transmission, and the technology for each is well developed. For example, design choices for performance parameters for power transmission cables, including conductor size and insulation requirements are well known. Likewise, design choices for performance parameters for signal transmission cables, such as signal speed, impedance, and shielding level, are equally well known.

For either power cables or signal transmission cables, two basic cable types are known: round and flat. Round cables are formed by the twisting, or "cabling" together of a plurality of individual insulated and/or shielded wires into an overall-jacketed cable having a generally round cross section. Flat cables are typically made by feeding a plurality of wires, each of which may be insulated and/or shielded (e.g., coaxial signal wires), into in a spaced apart, parallel arrangement, and held in such an arrangement by an overall jacket. Overall jackets for both round and flat cables are typically extruded on inline with the cable production.

In some cases, it is desirable to make a flat cable comprising flat conductors. In this type of cable, the conductors themselves have a flat, generally rectangular cross section. Such cables find use in such applications as board-to-board interconnections for electronic equipment, for example. The relatively low profile and greater flex life (for dynamic applications) make flat conductor flat cables ideal for these and many other applications. Examples of flat conductors cables include those manufactured and marketed by Axon Cable and Interconnect as Axojump® flat flexible cables.

One drawback to known methods of forming flat cables is production speed, particularly with small gauge conductors (e.g., below 36 AWG equivalent). For high quality cables it is required that each of the conductors feeding into the cable be held at a uniform tension, and spacing must be carefully maintained. As conductor size decreases (i.e., AWG increases), this requirement becomes more critical, and high production speeds are more difficult to achieve.

In addition to the problems of forming flat cables described above, for known methods of making flat cables comprising flat conductors, cost is a major factor. For many reasons, including technical complexity and relatively low usage, flat conductors are more expensive than round conductors, for equivalent gauge size.

Accordingly, it would be desirable to have a method of economically manufacturing flat cables for electrical power or signal transmission.

Additionally, it would desirable to have a method of economically manufacturing flat cables comprising flat conductors.

BRIEF SUMMARY OF THE INVENTION

An electrical cable of the present invention comprises a plurality of spaced, parallel flat conductors. Each of the plurality of flat conductors was previously integral with each immediately adjacent flat conductor. A dielectric material holds the conductors in the spaced, parallel relationship. The dielectric material can be a polymer film, a nonwoven, or other polymer materials such as PTFE, or expanded PTFE.

The cable of the present invention is made by providing first and second webs of dielectric materials and a third sheet of conductive material. The first and second web materials are bonded to the third sheet of conductive material in a face-to-face layered relationship thereby forming a bonded laminate. The bonded laminate is then incrementally stretched to separate the sheet of conductive material in to spaced, parallel flat conductors.

BRIEF DESCRIPTION OF THE DRAWINGS

While the specification concludes with claims pointing out and distinctly claiming the present invention, it is believed the same will be better understood by the following drawings taken in conjunction with the accompanying specification wherein like components are given the same reference number. Note that the Figures are not meant to represent relative scale and dimensions of any elements of the present invention.

DETAILED DESCRIPTION OF THE INVENTION

Figure 1:
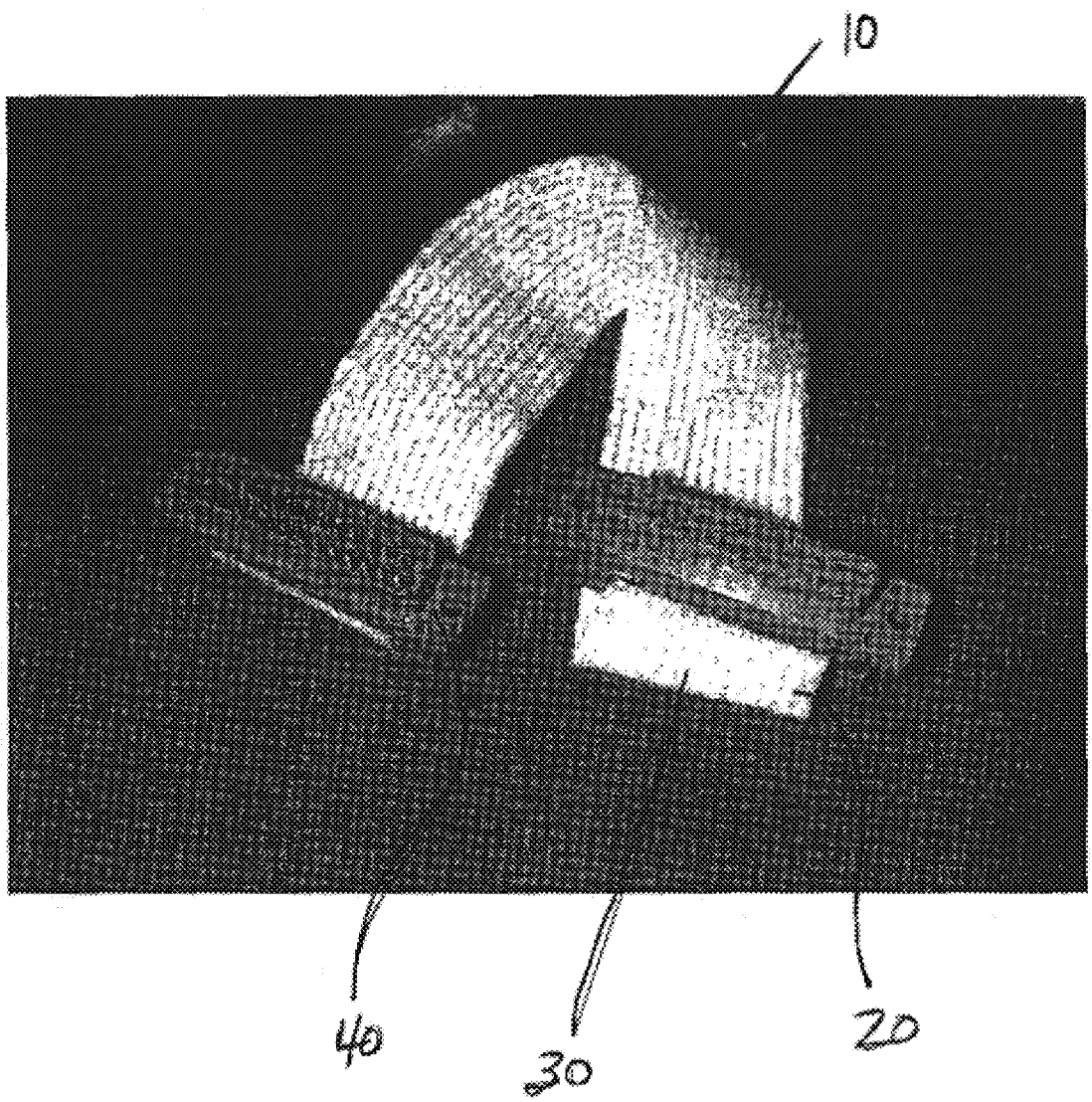
FIG. 1 is a perspective of one embodiment of a flat conductor cable of the present invention.

As used herein, the term "film" or "polymer film" is used to describe liquid impervious thermoplastic polymer films as are known in the art. Such films are typically thin films supplied as webs. Typical materials for such films include, without limitation, polyethylene, polypropylene, polyester, and blends thereof. Such films can be rendered liquid pervious by known methods such as aperturing. Such films can also be microporous and/or "breathable" to permit gas and vapors to penetrate, while remaining essentially liquid pervious.

As used herein, the term "nonwoven web" is used in its plain meaning as understood in the art and refers to a web that has a structure of individual fibers or threads which are interlaid, but not in any regular, repeating manner. Nonwoven webs have been, in the past, formed by a variety of processes, such as, for example, meltblowing processes, spunbonding processes and bonded carded web processes.

As used herein, the term "microfibers" refers to small diameter fibers having an average diameter not greater than about 100 microns.

As used herein, the term "meltblown fibers", refers to fibers formed by extruding a molten thermoplastic material through a plurality of fine, usually circular, die capillaries as molten threads or filaments into a high velocity gas (e.g., air) stream which attenuates the filaments of molten thermoplastic material to reduce their diameter, which may be to a microfiber diameter. Thereafter, the meltblown fibers are carried by the high velocity gas stream and are deposited on a collecting surface to form a web of randomly dispersed meltblown fibers.

As used herein, the term "spunbonded fibers" refers to small diameter fibers that are formed by extruding a molten thermoplastic material as filaments from a plurality of fine, usually circular, capillaries of a spinneret with the diameter of the extruded filaments then being rapidly reduced by drawing.

As used herein, the term "unitary web" refers to a laminate of two or more webs of material, including polymer films and nonwoven webs, that are sufficiently joined, such as by thermal bonding means, to be handled, processed, or otherwise utilized, as a single web.

As used herein, the term "polymer" generally includes, but is not limited to, homopolymers, copolymers, such as, for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to, isotactic, syndiaotactic and random symmetries.

As used herein, the term "elastic" refers to any material which, upon application of a biasing force, is stretchable, that is, elongatable, at least about 60 percent (i.e., to a stretched, biased length, which is at least about 160 percent of its relaxed unbiased length), and which, will recover at least 55 percent of its elongation upon release of the stretching, elongation force. A hypothetical example would be a one (1) inch sample of a material which is elongatable to at least 1.60 inches, and which, upon being elongated to 1.60 inches and released, will recover to a length of not more than 1.27 inches.

Many elastic materials may be elongated by more than 60 percent (i.e., much more than 160 percent of their relaxed length), for example, elongated 100 percent or more, and many of these materials will recover to substantially their initial relaxed length, for example, to within 105 percent of their initial relaxed length, upon release of the stretch force. Such materials are denoted herein by the term "highly elastic" which refers to any material which upon application of a biasing force, is stretchable, that is, elongatable, at least about 200 percent (i.e., to a stretched, biased length, which is at least about 300 percent of its relaxed unbiased length), and which, will to within 105 percent of their initial relaxed length, upon release of the stretch force. Therefore, highly elastic materials are generally also elastic, but not all elastic materials are highly elastic.

As used herein, the term "nonelastic" refers to any material which does not fall within the definition of "elastic" above.

As used herein, the term "elongation to break" refers to the percent elongation a material exhibits under an applied tensile loading before complete break, i.e., complete failure in tension.

As used herein, the term "extensible" refers to any material which, upon application of a biasing force, is elongatable, at least about 25 percent without experiencing catastrophic failure. Catastrophic failure includes substantial tearing, fracturing, rupturing, or other failure in tension such that, if tested in a standard tensile tester, the failure would result in a sudden significant reduction in tensile force. As used herein, the term "highly extensible" refers to any material, which upon application of a biasing force is elongatable, at least about 100 percent without experiencing catastrophic failure.

As used herein, the term "machine direction" is used as is commonly known in the art, and refers to the longitudinal direction of a web material being processed. "cross-direction" is likewise used as is commonly known in the art, and refers to a direction orthogonal and in the same plane as the machine direction. In a finished article made from such webs, the terms machine direction and cross-direction refer to the respective directions of the precursor web, prior to forming into the finished article.

One embodiment of a flat cable of the present invention is shown in FIG. 1. As shown in FIG. 1, the flat cable 10 comprises a plurality of spaced, parallel conductors 30, which are held in a spaced relationship by a dielectric material 20 which may be an intermediate dielectric material, or the overall jacketing material. The cable 10 can be attached to standard or custom connectors 40 by known methods.

The conductors 30 can be copper, aluminum, gold, silver, or other conductive metal, and are preferably at least partially tin plated copper. The conductor-to-conductor spacing, hereinafter referred to as the "pitch" can be varied as desired, up to the limit of the extensibility of the dielectric material 20 as described below. In general, the pitch can range from 0.50 mm to 2.44 mm. For example, the pitch can be 0.50 mm, 0.80 mm, 1.00 mm, 1.25 mm, 1.27 mm, 2 mm or 2.45 mm. Additionally, the pitch can be varied throughout the cable.

The total number of conductors 30 in the cable 10 is limited only by the size of the supply material and the apparatus dimensions, as described below. However, in general, the number of conductors can range from 2 to 1000.

Figure 2:
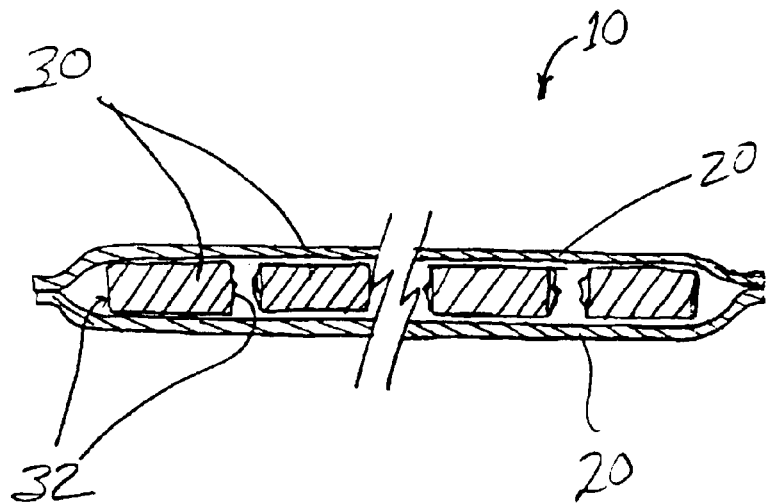
FIG. 2 is a cross-sectional view of a portion of the flat conductor cable shown in FIG. 1.

As shown in FIG. 2, the conductors have a flat, generally rectangular cross section. The long dimension of the cross section is referred to herein as the conductor width and the short dimension of the cross section is referred to herein as the conductor thickness. Both the conductor width and thickness can be varied, and each is limited only by the material characteristics of the conductor material and the apparatus dimensions as described below. In general, however, the width can be selected based on the conductor thickness to arrive at a desired equivalent gauge size (i.e., AWG). In general, for known useful applications, such as in the automobile industry, the thickness can range from 0.05 mm to 0.076 mm. For example, the conductor thickness can be 0.05 mm, 0.10 mm, 0.035 mm, or 0.076 mm. Likewise, the conductor width range can from 0.10 mm to 1.5 mm, in 0.10 mm increments.

As shown in FIG. 2, due to the method of making the cable of the present invention, the conductors 30 closely approximate a rectangular cross section. Near their longitudinal edges 32 the profile is defined by the mode of failure of the conductive material desired in the manufacturing technique of the present invention as disclosed below. While this profile can vary, and may be almost imperceptible, it is noted that width and thickness dimensions can be considered as "average width" or "average thickness" for a given conductor, and these values will closely approximate the overall thickness or width value.

If plated conductors, such as tin plated copper, are used, the process for making a cable 10 of the present invention also results in conductors 30 that are not fully plated. For reasons that will be apparent after disclosure of the method of making, the conductors 30 of the present invention have portions along their respective lateral edges 32 that do not have plating. While this is a result of the manufacturing process, it is not considered detrimental to the operation of the cables for power or signal transmission properties.

Figure 3:
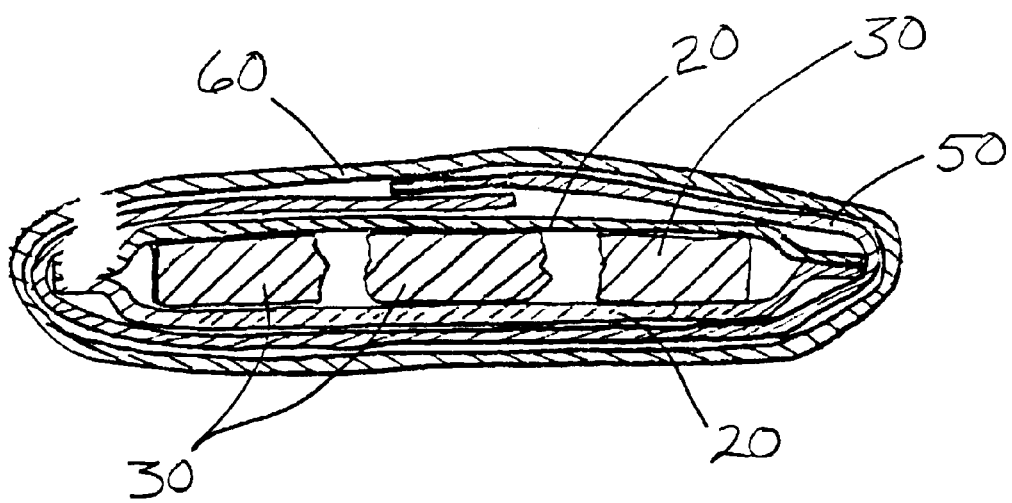
FIG. 3 is a cross-sectional view of another embodiment of a flat conductor cable of the present invention.

The cable 10 of the present invention can be electrically shielded by known methods. For example, as shown in FIG. 3, a shield 50 comprising an aluminum foil, or polyester/aluminum foil laminate can be wrapped around the cable 10 to provide 360 degree coverage. This shield can be grounded to one or several conductors by welding. The foil can be longitudinally wrapped, or spirally wrapped, as is known in the art. In another embodiment, the shield 50 can be applied by braiding on a shield comprising a plurality of relatively small gauge wires, by methods known in the art.

With reference to FIG. 3, the cable of the present invention can be protected from external physical influences by a jacket 60, which can be any known extruded polymeric material, depending on the end use design requirements.

The dielectric material 20 can be chosen from known materials supplied as films or webs. The dielectric material could be a woven fabric. Dielectric material 20 can be polyester, polyethylene, polypropylene, PVC, or other films. Representative films and their respective dielectric constants suitable for use in the present invention are listed in Table 1 below. A particularly preferred material is one that, upon incrementally stretching at a sufficient rate and/or temperature, exhibits a reduced density, and consequently, a reduced dielectric constant. For example, microporous films can be made by incrementally stretching talc filled polypropylene. Thus, the resulting dielectric constant is expected to be less than 2.6. Likewise, PTFE, once expanded to reduce its density, can have a dielectric constant of 1.3 to 1.8.

TABLE 1

Representative Dielectric Materials

| Material | Dielectric Constant |
|---|---|
| Polytetrafluoroethylene (PTFE) | 2.1 |
| Nylon 12, Film Grade | 2.7 |
| Low Density Polyethylene (LDPE), Film Grade | 2.3 |
| High Density Polyethylene (HDPE), Film Grade | 2.3 |
| Polypropylene with 40% talc filler | 2.4 |
| Polypropylene with 50% mica filler | 3 |

Preferably the dielectric materials 20 are sufficiently bonded to the conductor material prior to processing by the method disclosed below. By "sufficiently" is meant that the bond is strong enough to hold the conductor material 30 in place relative to the dielectric material 20 during processing of the cable 10 as described below. Otherwise, no particular bond type, bond strength, adhesive type, or adhesive level is considered limiting to the present invention. One particularly good dielectric material 20 is film grade polyethylene which, due to its thinness and relatively good dielectric properties, makes an excellent dielectric material for thin, lightweight, flat cables.

In another embodiment, rather than bonding the conductor material 30 to the dielectric material, the conductor material can be directly coated onto the dielectric material, such as by sputtering, vacuum deposition or other known means.

The dielectric material 20 can be in the form of nonwoven, expanded, foamed, or other air-containing materials, as long as the material has a higher elongation to break in at least one direction than the conductor material, and maintains sufficient integrity after processing as disclosed below to maintain adequate conductor spacing during further processing or use of the cable. "Adequate" conductor spacing depends on the end use of the cable. For example, for power cables, maintenance of precise conductor spacing is not critical, but for impedance-controlled signal cables, precise conductor spacing can be critical.

Dielectric material 20 can comprise nonwoven materials, which is the material shown on cable 10 in FIG. 1. Nonwoven materials can be made of polymer fiber wherein the polymer itself has a low dielectric constant. Due to the inherent low density and high air content of nonwoven materials, such materials make very good dielectric materials for signal transmission cables, for example. Nonwoven materials of the present invention can be supplied as a web, and can be a spunbonded web, a meltblown web, or a bonded carded web. If the nonwoven web is a web of meltblown fibers, it may include meltblown microfibers. The nonwoven web can be made of fiber forming polymers such as, for example, polyolefins. Exemplary polyolefins include one or more of polypropylene, polyethylene, ethylene copolymers, propylene copolymers, and butene copolymers. The dielectric material (prior to processing by the method of the present invention), can have a basis weight of between 10 gram per square meter (gsm) and 120 gsm, and can be between about 30 gsm and 60 gsm.

In general, for nonwoven, foamed and expanded materials, the less polymer (and, conversely, the more air) in between conductors, the higher the signal speed of the electrical signal (i.e., the velocity of propagation). This well-known physical principal can be applied in the selection of the dielectric material 20 of the present invention. For example, for high-speed transmission of electrical signals, a low-dielectric constant material, such as polytetrafluoroethylene (PTFE, dielectric constant=2.1), and preferably expanded PTFE (e.g., GORE-TEX®, dielectric constant= 1.3–1.9, available from W. L. Gore and Associates, Newark, Del. USA) can be used as the dielectric material 20. The expanded PTFE can be "etched" using known techniques to facilitate bonding. Alternately, a calcium carbonate filled polyethylene (film grade, dielectric constant=2.4) can be used as the dielectric material. When stretched by the method of the present invention, such a material expands to form a lower density, microporous network, which results in a lower dielectric constant.

Bonding of the dielectric material 20 to the conductor prior to processing into cable 10 can be accomplished by known methods. In general, it is advantageous to use the minimum amount of adhesive sufficient to ensure adequate bonding of the conductors to the dielectric material, such that the electrical characteristics, such as signal fidelity, are not adversely affected. Specialty adhesives can be used, such as adhesives available from Lepercq, SA, Chassiux Cedex, France. Hot melt adhesives can also be used, such as H-2031 available from Ato-Findley, Wauwatosa, Wis.

The dielectric material 20 has a percent elongation to break value greater than that of the conductive sheet 130 as shown below. The conductive sheet 130 is transformed from an integral sheet into the individual conductors 30. If more than one dielectric layer is used, then at least one should have a percent elongation to break value greater than that of the conductor 30. In general, the integral conductor material 130 is supplied as a thin sheet or foil of conductive metal, such as a copper foil, which can have an elongation to break less than about 10%. The dielectric material can be a polymer material that is extensible or highly extensible, thereby exhibiting an elongation to break greater than 25%.

Thus, in one aspect, the present invention can be described as an electrical cable comprising a plurality of spaced, parallel flat conductors, each of the plurality of flat conductors having been previously integral with each immediately adjacent flat conductor. Of course, "previously integral" in this context means previously with respect to the process of forming the electrical cable from an integral web or sheet of metal. Thus, prior to forming into individual conductors, each conductor so formed was integral with adjacent conductors as a unitary, integral sheet or web. The term "previously integral" does not mean previously integral in an abstract sense of having been integral at an unidentified time in the past, as copper ore, for example.

Method of Making

Figure 4:
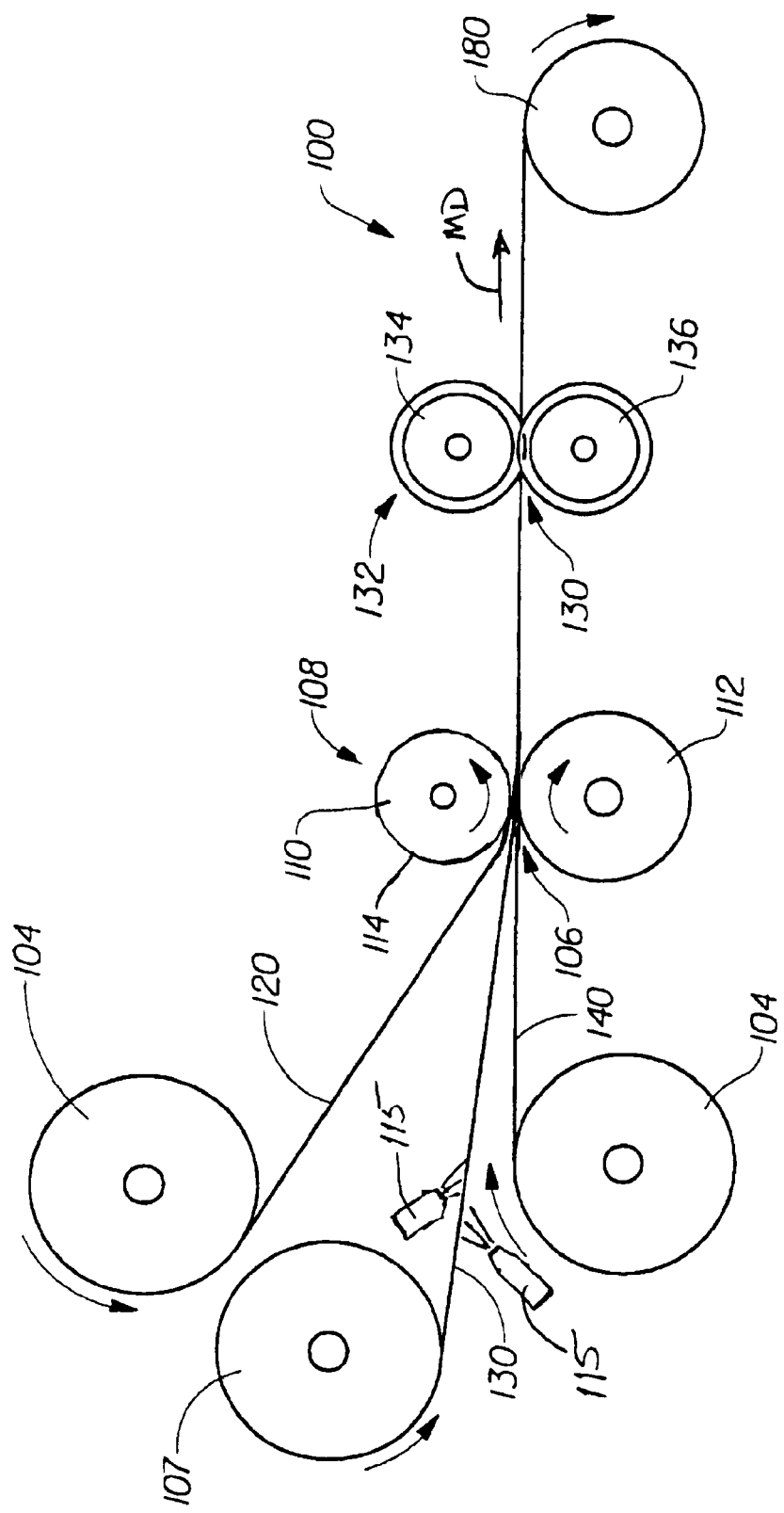
FIG. 4 is a schematic representation of a process for making a flat conductor cable of the present invention.

Referring to FIG. 4 there is schematically illustrated at 100 a process making a cable 10 of the present invention.

A first web 120 of relatively extensible dielectric material 20, is unwound from a supply roll 104 and travels in a direction indicated by the arrows associated therewith as the supply roll 104 rotates in the direction indicated by the arrows associated therewith. Likewise a second web 140 of relatively extensible web of relatively extensible dielectric material 20 (which can be the same or different type of dielectric material 20 from that which comes from supply roll 104) is unwound from supply roll 105. A conductive sheet 130, which can be a relatively inextensible (with respect to first and second webs 120, 140) metal sheet or web, is likewise drawn from supply roll 107. The three components pass through a nip 106 of the bond roller arrangement 108 formed by rollers 110 and 112. Conductive sheet 130 can be non-metal, such as a conductive polymer sheet, for example.

In one embodiment, both first and second webs 120, 140 comprise nonwoven materials, and are identical. The nonwoven material may be formed by known nonwoven extrusion processes, such as, for example, known meltblowing processes or known spunbonding processes, and passed directly through the nip 106 without first being bonded and/or stored on a supply roll. However, in a preferred embodiment, the nonwoven webs are consolidated webs commercially available on supply rolls.

In another embodiment, both first and second webs 120, 140 comprise polymer film materials, and are identical. The film material can be any of thin films known in the art for their electrical insulating or dielectric properties. For example, polyethylene, polyester, PVC and polyamide films can be used. Likewise, non-thermoplastic films, including PTFE films and expanded PTFE films can be used. In one embodiment, a PTFE web having a basis weight of about 60 gsm is used, and the temperature, pressure, and line speed of the incremental stretching system described below simultaneously expands the PTFE and separates the conductor sheet 130 into the spaced, parallel conductors 30 of cable 10.

The first and second web 120, 140 materials can be nonelastic, extensible, or highly extensible, and, under certain conditions can be elastic or highly elastic. The only restriction is that the first and second web 120, 140 materials do not elastically recover fully after the incremental stretching step described below. That is, once the conductive sheet material 130 has been processed into a plurality of spaced, parallel conductors, the first and second web 120, 140 materials should not elastically recover to the extent that the spaced conductors are no longer sufficiently spaced. In particular, adjacent conductors should not be touching. The first and second web 120, 140 materials may themselves be a multilayer material comprising, for example, at least one layer of a nonwoven web joined to at least one layer of a thermoplastic polymer film.

Referring to FIG. 4, the bond roller arrangement 108 preferably comprises a calendar roller 110, which can be a patterned calendar roller, and a smooth anvil roller 112. The nip gap, as well as the pressure applied by rollers 110 and 112, is controlled by well known means in the art. The gap and pressure need only be sufficient to ensure sufficient bonding of the layers, but can be set to also effect a predetermined amount of compression, if desired.

One or both of the calendar roller 110 and the smooth anvil roller 112 can be heated and the temperature of either roller and the pressure between the two rollers may be adjusted by well known means to provide the desired temperature, if any, and pressure to effect bonding of the first and second webs 120, 140 to the conductive sheet 130 in a composite laminate. The laminate comprises the conductive sheet 130 "sandwiched" between first and second webs 120, 140.

The calendar roller 110 can be a patterned or smooth right circular cylinder of steel. Anvil roller 112, is likewise a smooth surfaced, right circular cylinder of steel.

Prior to passing through nip 106, adhesive can be applied to the first and second webs 120, 140, or to conductive sheet 130. As shown in FIG. 4, in one embodiment, hot melt adhesive is applied by spraying to both sides of sheet 130 by adhesive application means 115. Any adhesive application means known in the art can be used, including extrusion, wiping, spraying, and slot coating. The amount and pattern of adhesive application can be adjusted as necessary to ensure that, once conductors 30 are formed, each conductor is sufficiently bonded to the adjacent dielectric material to prevent undesired movement of the conductor relative to the dielectric material.

After passing through nip 106, the composite laminate passes through nip 130 formed by an incremental stretching system 132 employing opposed pressure applicators 134 and 136 having three-dimensional surfaces which at least to a degree are complementary to one another. It is the incremental stretching system 132 that separates the conductive sheet 130 into discrete, spaced, parallel conductors 30 of cable 10. This is because the first and second webs 120, 140 are relatively extensible, so that they extend during the incremental stretching, and remain extended to a sufficient degree to hold the conductors 30 in the discrete, spaced, parallel relationship. However, the conductive sheet 130 is relatively non-extensible, and separates into strips which make up the individual conductors 30 upon application of the incremental extension forces. The separation is smooth, uniform, and can be carried out at relatively high speeds suitable for commercial production.

Figure 5:
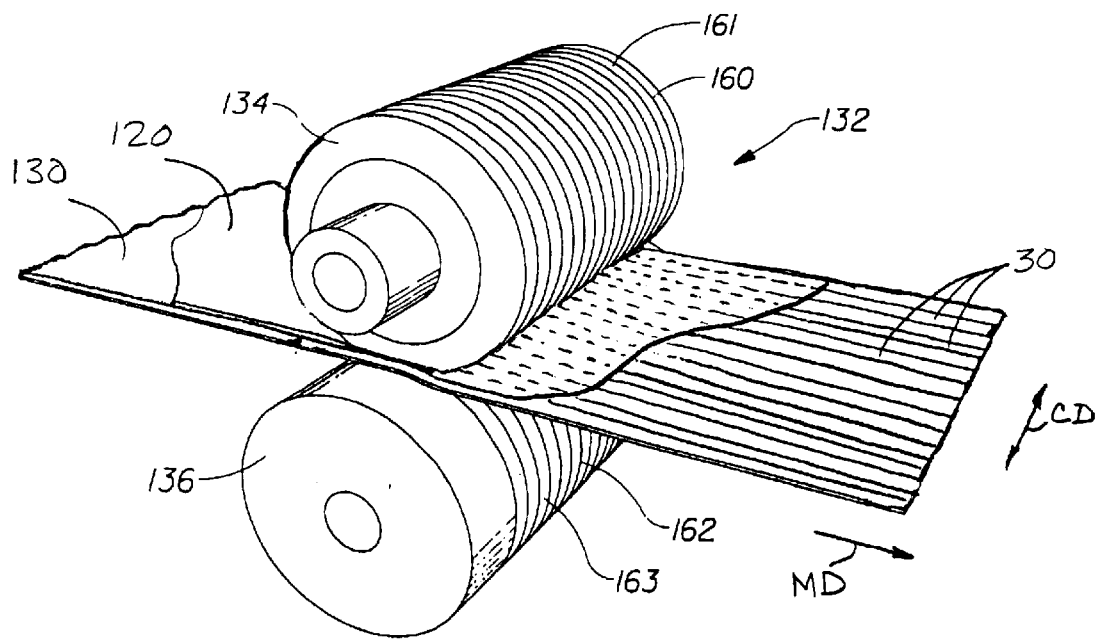
FIG. 5 is a perspective view of an apparatus for stretching a laminate of the present invention to a flat conductor cable of the present invention.
Figure 6:
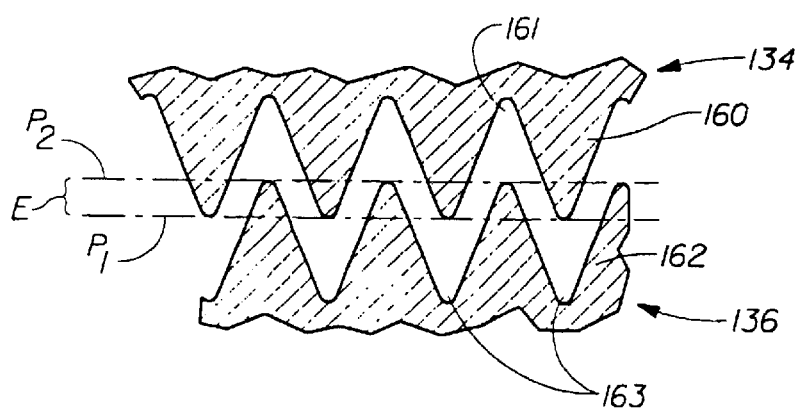
FIG. 6 is a cross-sectional view of a portion of the mating portions of the apparatus shown in FIG. 5.

Referring now to FIG. 5, there is shown a fragmentary enlarged view of the laminate web being processed by the incremental stretching system 132 comprising incremental stretching rollers 134 and 136. The incremental stretching roller 134 includes a plurality of teeth 160 and corresponding grooves 161 which extend about the entire circumference of roller 134. Incremental stretching roller 136 includes a plurality of teeth 162 and a plurality of corresponding grooves 163. The teeth 160 on roller 134 intermesh with or engage the grooves 163 on roller 136, while the teeth 162 on roller 136 intermesh with or engage the grooves 161 on roller 134. The teeth of each roller are generally triangular-shaped, as shown in FIG. 6. The apex of the teeth may be slightly rounded, if desired for certain material requirements.

FIG. 6 shows a portion of the intermeshing of the teeth 160 and 162 of rollers 134 and 136, respectively. The term "pitch" as used herein with reference to incremental stretching system 132, refers to the distance between the apexes of adjacent teeth. The pitch can be between about 0.02 to about 0.30 inches, and is preferably between about 0.05 and about 0.15 inches. The height (or depth) of the teeth is measured from the base of the tooth to the apex of the tooth, and is preferably equal for all teeth. The height of the teeth can be between about 0.10 inches and 0.90 inches, and is preferably about 0.25 inches and 0.50 inches.

The teeth of the respective rollers can be partially intermeshing. The degree to which the teeth on the opposing rolls intermesh is referred to herein as the "depth of engagement" or "DOE" of the teeth. As shown in FIG. 6, the DOE, E, is the distance between a position designated by plane P1 where the apexes of the teeth on the respective rolls are in the same plane (0% engagement) to a position designated by plane P2 where the apexes of the teeth of one roll extend inward beyond the plane P1 toward the valley on the opposing roll.

As the composite laminate passes through the incremental stretching system 132 it is subjected to tensioning in the CD or cross-machine direction causing the composite laminate to be extended in the CD direction. Thus, the mechanism of discrete conductor production is tensile separation, as opposed to shearing. Shearing of the conductors would not provide for conductor spacing, and would destroy the integrity of the dielectric layer. However, the stretching induced by the incremental stretching system 132 in effect "pulls apart" the conductive web or sheet 130 into the individual conductors 30. It can be seen that each individual flat conductor 30 was previously integral with each immediately adjacent flat conductor 30. As used herein the term "integral" is used to mean "one", i.e., not made up of constituent parts joined together.

The pitch, conductor width, and spacing of conductors 30 is determined by the particular pitch, or distance between the apexes, of adjacent teeth 160 and 162 of rollers 134 and 136, respectively, the DOE, E, and the material properties of the webs 120, 130 and 140 of the composite laminate being incrementally stretched. Therefore, the examples listed below are considered exemplary, and not limiting.

The cable of the present invention, after processing as shown above, can be further processed to have additional shielding and/or jacketing components, as is known in the art. However, in one embodiment, the outer nonwoven dielectric materials are sufficient to be the outer jacketing materials as well. Such a cable is suitable for controlled environment applications, where fluid pervious, mechanically tough jacketing characteristics are not required.

The cable of the present invention finds use in industry, such as in automotive applications, including, for example for a steering wheel rotary connector, connections to control panels, such as in car radios, antennae connections, door cables, cables inside headliners, and other areas where low profile, flexible cables offer an advantage. The cable also finds use as a resistive heating element, useful, for example, for wrapping water pipes to prevent freezing. The cable can also find use in sensor materials or devices (e.g., pressure sensing fabrics), electrostatic discharge materials or devices, antennas, heat shielding, and conductive fabrics. Moreover, if a breathable dielectric material is used, cables of the present invention with nonwoven dielectric/insulation can be used in body-contacting electrical applications, where user comfort is desirable. For example, disposable diaper with sensors, or medical applications requiring skin contact with electrically conductive instrumentation can benefit by a clothlike, soft, breathable cable of the present invention.

The cable shown in FIG. 1 is described now as by way of example. The conductors 30 were made from a conductive layer consisting of a 65 gsm aluminum food wrap material, available from the Reynold's Metal Products Co. Two dielectric layers were used, one on each side of the conductive layer. Both dielectric layers consisted of 30 gsm polyethylene nonwoven available from BBA Nonwoven, Greenville, S.C. The adhesive used to bond the dielectric layers 20 to the conductive sheet was M77 spray adhesive available from 3M, Minneapolis, Minn. applied in a light, even coat. The three constituent layers were pressed together under light pressure using a hand roller to sufficiently bond the layers together.

The laminate was then subjected to incremental stretching via the incremental stretching apparatus described above. The tooth pitch of each of the interengaging rollers was 0.060 inches, and the DOE was 0.085 inches. The laminate was processed through the incremental stretching apparatus by hand at approximately 10 feet per minute.

The resulting cable had 14 conductors 30, each approximately 1.5 mm wide, and spaced on a pitch of approximately 2 mm. Individual continuity tests were performed on each of the 14 conductors, confirming the integrity of each. Additionally, the regular spacing between adjacent conductors prevented unwanted contact between adjacent conductors.

While particular embodiments of the present invention have been illustrated and described, it would be obvious to those skilled in the art that various other combinations and modifications can be made without departing from the scope of the invention. For example, rather than use two webs 120 and 140, it may be beneficial to simply use one of 120 or 140. The process would otherwise be identical, with the finished flat cable 10 only having a dielectric material on one side thereof. However, this may be sufficient for many applications, and it nevertheless can be further insulated, such as by extrusion of a polymer jacket. It is therefore intended to cover in the appended claims all such combinations and modifications that are within the scope of this invention.

What is claimed is:

1. An electrical cable comprising:

a) a plurality of spaced, parallel flat conductors and b) at least one web of dielectric material, wherein said web of dielectric material is unstretched in regions containing said conductors and said web of dielectric material is stretched in regions not containing said conductors to hold said conductors in said spaced, parallel relationship.

2. The electrical cable of claim 1, wherein said conductors are metal.

3. The electrical cable of claim 1, wherein said dielectric material comprises a polymer.

4. The electrical cable of claim 1, wherein said dielectric material comprises a nonwoven.

5. The electrical cable of claim 1, wherein said dielectric material comprises polytetrafluoroethylene.

6. The electrical cable of claim 1, wherein said dielectric material comprises expanded polytetrafluoroethylene.

7. The electrical cable of claim 1, wherein said dielectric material comprises microporous film.

* * * * *